US00PP31695P3

(12) United States Plant Patent
Wu et al.

(10) Patent No.: US PP31,695 P3
(45) Date of Patent: Apr. 21, 2020

(54) BERMUDAGRASS PLANT NAMED 'OKC 1131'

(50) Latin Name: ***Cynodon dactylon* var. *dactylon* Pers. accession A12268 x *C. transvaalensis* Burtt-Davy OSU selection '2747'**
Varietal Denomination: OKC 1131

(71) Applicant: The Board of Regents for Oklahoma State University, Stillwater, OK (US)

(72) Inventors: Yanqi Wu, Stillwater, OK (US); Dennis L. Martin, Stillwater, OK (US); Justin Q. Moss, Stillwater, OK (US); Nathan R. Walker, Stillwater, OK (US); Charles Fontanier, Stillwater, OK (US)

( * ) Notice: Subject to any disclaimer, the term of this patent is extended or adjusted under 35 U.S.C. 154(b) by 0 days.

(21) Appl. No.: 15/932,946

(22) Filed: May 25, 2018

(65) Prior Publication Data

US 2019/0364715 P1 Nov. 28, 2019

(51) Int. Cl.
*A01H 5/12* (2018.01)
*A01H 6/46* (2018.01)

(52) U.S. Cl.
USPC ..... Plt./389
CPC ..... *A01H 6/4612* (2018.05)

(58) Field of Classification Search
USPC ..... Plt./389
CPC ... A01H 5/12; A01H 5/00; A01H 5/02; A01H 5/10; A01H 6/46
See application file for complete search history.

(56) References Cited

U.S. PATENT DOCUMENTS

| | | | | | |
|---|---|---|---|---|---|
| PP8,162 | P * | 2/1993 | Keen | | Plt./389 |
| PP8,168 | P * | 3/1993 | Keen | | Plt./389 |
| PP11,181 | P * | 1/2000 | Riley | | Plt./389 |
| PP16,801 | P2 * | 7/2006 | Taliaferro | A01H 5/12 | Plt./389 |
| PP18,247 | P3 * | 11/2007 | Parsons | A01H 5/12 | Plt./389 |
| PP24,271 | P3 * | 2/2014 | Wu | A01H 5/12 | Plt./389 |

OTHER PUBLICATIONS

Sod Production Services. New Turf Bermudagras 'OKC 1131' 2019, retrieved on May 2, 2019, retrieved from the Internet at https://www.sodproductionservices.com/tahoma-31-bermudagrass/new-bermuda-grass-okc-1131/, 3 pp. (Year: 2019).*

Upov Pluto Plant Variety Database May 1, 2019, retrieved on May 2, 2019, retrieved from the Internet at https://www3.wipo.int/pluto/user/en/index.jsp, one page. (Year: 2019).*

* cited by examiner

*Primary Examiner* — June Hwu
(74) *Attorney, Agent, or Firm* — Dunlap Codding, P.C.

(57) ABSTRACT

'OKC 1131' is a new clonally propagated F1 hybrid from a cross of *Cynodon dactylon* var. *dactylon* accession A12268 (2n=4x=36) x *C. transvaalensis* Oklahoma State University (OSU) section '2747' (2n=2x=18). The distinct variety has exceptional winter survivability, improved drought resistance, superior traffic tolerance, high turf quality, and wide adaptation. It has very short internodes and leaf blades. It has demonstrated the characteristics of fast establishment rate, early green up, dark green color, and sufficient sod tensile strength for reliable sod production on farm.

6 Drawing Sheets

STATEMENT REGARDING FEDERALLY FUNDED RESEARCH OR DEVELOPMENT

This invention was made in part with government support under grants NO. 2010-51181-21064 and NO. 2015-51181-24291 by the USDA NIFA. The government has certain rights in the invention.

Latin name of the genus and species of the plant claimed: *Cynodon dactylon* var. *dactylon* Pers. accession A12268 x *C. transvaalensis* Burtt-Davy OSU selection '2747'.

Variety denomination: 'OKC 1131'.

CROSS REFERENCE TO RELATED APPLICATIONS

Not Applicable.

BACKGROUND

The present invention relates to a new and distinct cultivar turf bermudagrass named 'OKC 1131' and is hereinafter referred to by its cultivar name 'OKC 1131'.

'OKC 1131' is a clonally propagated interspecific triploid hybrid (2n=3x=27) from a cross of *Cynodon dactylon* var. *dactylon* accession A12268 (2n=4x=36) x *C. transvaalensis* Oklahoma State University (OSU) selection '2747' (2n=2x=18)—accordingly, 'OKC 1131' does not produce seed. *Cynodon dactylon* var. *dactylon* accession A12268 (2n=4x=36) is a common bermudagrass which was crossed with *C. transvaalensis* Oklahoma State University (OSU) selection '2747' (2n=2x=18), an African bermudagrass. The cultivar will be marketed as an "interspecific turf bermudagrass, *Cynodon dactylon* var. *dactylon* Pers. accession A12268 x *C. transvaalensis* Burtt-Davy OSU selection '2747'." The *Cynodon dactylon* var. *dactylon* accession A12268 and *C. transvaalensis* '2747' parents are no longer available for comparison.

'OKC 1131' is an asexually-reproduced interspecific turf bermudagrass, first developed by planting clonal plants of the two parents within close proximity, in a small crossing plot at the Oklahoma State University Agronomy Research Station in August 2006 in Stillwater, Okla. Stolons of 'OKC 1131' were regularly used in the vegetative propagation of 'OKC 1131'; however, sod and sprigs are presently utilized in the commercial production of 'OKC 1131'. Seeds were hand-harvested from their respective parents in the crossing block, and germinated in the summer of 2007. Seedlings from the harvested seed of this cross, as well as other crosses between other parent plants, were transplanted to a space-planted selection nursery (2008 Turf Bermudagrass Hybrid Selection Nursery) in July 2008. In the fall of 2010, 64 clonal plants were selected from the nursery; in 2011, the selected plants were entered into a regional trial with two replications at seven locations: Stillwater, Okla.; Dallas and College Station, Tex.; Gainesville Fla.; Raleigh, N.C.; Tifton and Griffin, Ga. In 2013, 'OKC 1131' was advanced to the 2013-2018 National Turfgrass Evaluation Program (NTEP) National Bermudagrass Test.

The NTEP test provided data from 17 locations in 2013 and 2014, and from 19 locations in 2015. 'Latitude 36' (tradename for 'OKC 1119' described and claimed in U.S. Plant Pat. No. 24,271), 'Tifway', 'Patriot' (described and claimed in U.S. Plant Pat. No. 16,801), and 'Celebration' (tradename for 'Riley's Super Sport' described and claimed in U.S. Plant Pat. No. 11,181) were utilized as comparative standard cultivars for vegetatively propagated entries in the national test. This multi-environment testing provided the most definitive data on the performance characteristics of 'OKC 1131' relative to other turf bermudagrass cultivars.

The distinctive traits of the variety have remained stable as the advanced generation clonal plants appear identical to the original plant in morphological phenotype and in genetic characteristics that have been measured.

SUMMARY OF THE INVENTION

'OKC 1131' bermudagrass produces a high-quality turf suitable for use where high quality turf is demanded and good management will be practiced on sites such as sports fields, golf courses, commercial properties, and high quality residential lawns. 'OKC 1131' bermudagrass is a distinct variety of bermudagrass which has exceptional winter survivability, improved drought resistance, superior traffic tolerance, high turf quality, and wide adaptation. 'OKC 1131' produces short internodes and leaf blades; has demonstrated the characteristics of fast establishment rate, early spring greenup, dark green color, and sufficient sod tensile strength for reliable sod production. These characteristics make 'OKC 1131' especially viable in a wide variety of climatic regions. 'OKC 1131' is highly sterile and is propagated asexually. 'OKC 1131' can be distinguished from other turf bermudagrass cultivars by morphological and/or genetic characteristics outlined herein.

BOTANICAL DESCRIPTION OF 'OKC 1131'

'OKC 1131' is a distinct cultivar from the interspecific cross of *Cynodon dactylon* var. *dactylon* Pers. accession A12268 x *C. transvaalensis* Burtt-Davy OSU selection '2747'. It was developed and vegetatively propagated by the Oklahoma State University Agronomy Research Station in Stillwater, Okla. Identifying morphological characteristics of 'OKC 1131' are its dark green color and fine texture. 'OKC 1131' does not produce seed. The color of the upper and lower surfaces of the 'OKC 1131' bermudagrass's leaves is classified as '144A' based on The R.H.S. Colour Chart and its inflorescence consists of 3 or 4 racemes with each raceme having a length of from about 1.3 cm to about 2.4 cm. 'OKC 1131's' growth is both stoloniferous and rhizomatous, but not bunch type.

Figure 1:
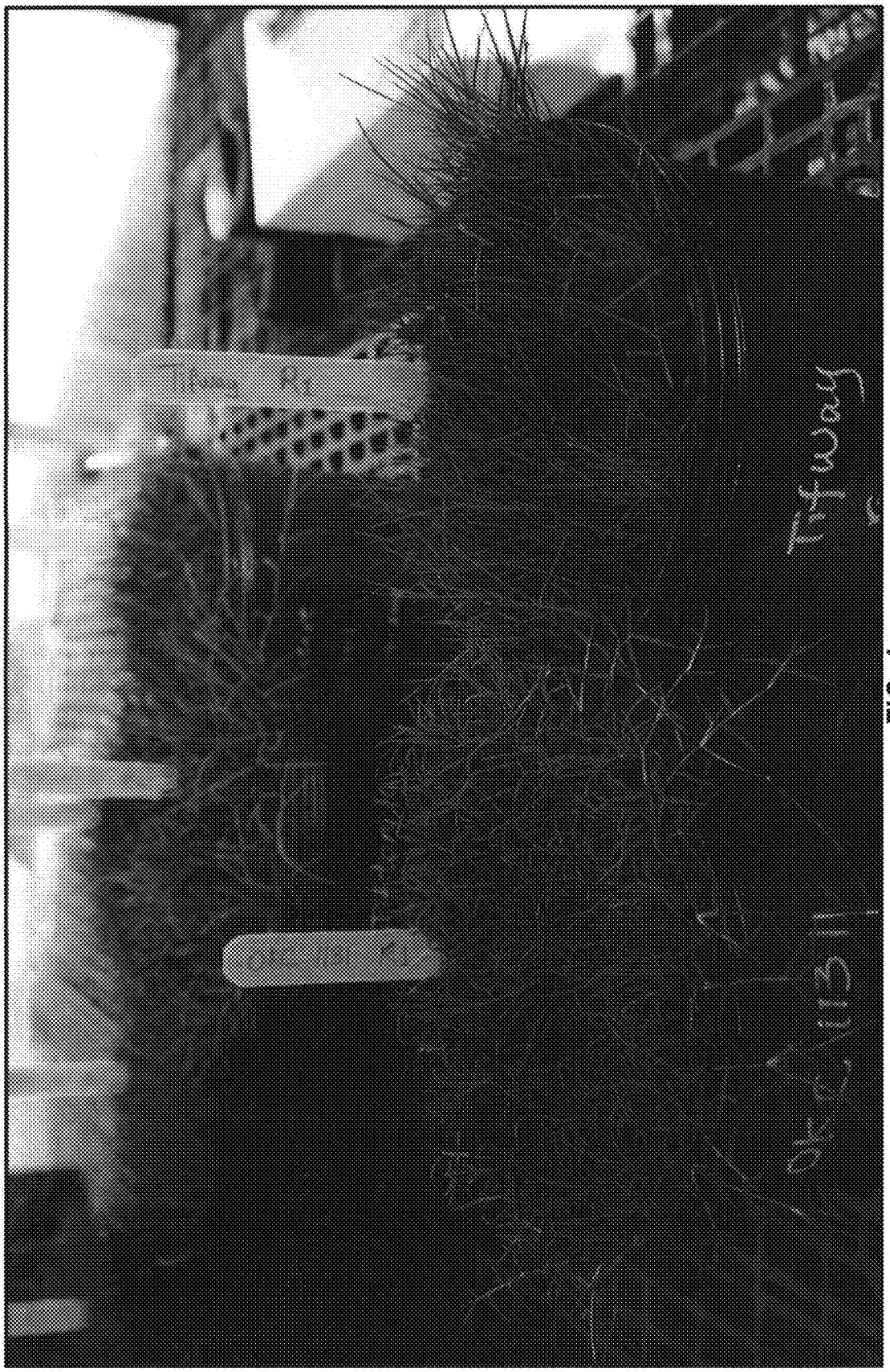
FIG. 1 is a comparative of mature growth 'OKC 1131' (location in image) to 'TIFWAY' (location in image).
Figure 2:
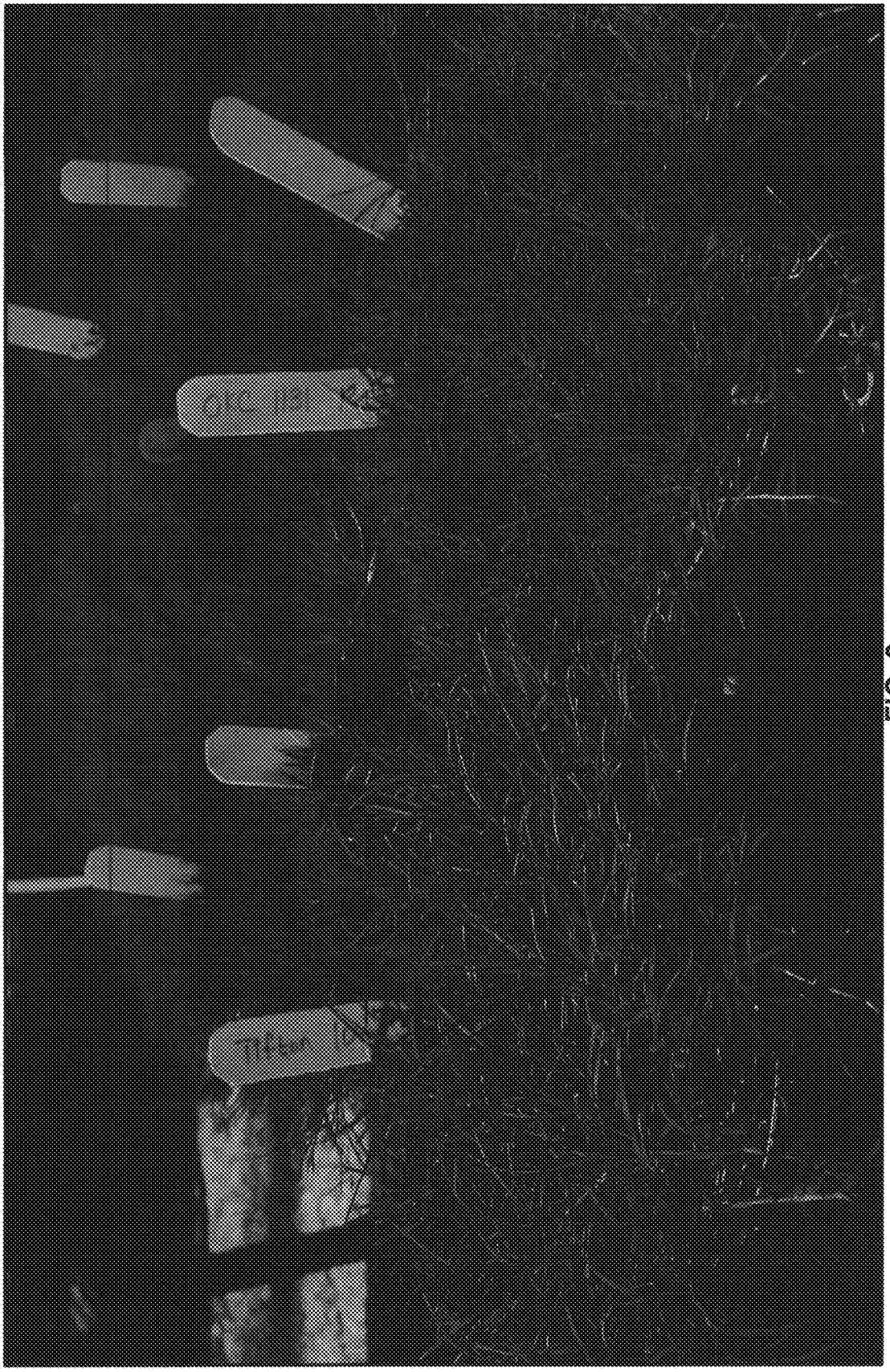
FIG. 2 is a comparative of mature growth 'OKC 1131' (right) to 'TIFTON 10' (left).
Figure 3:
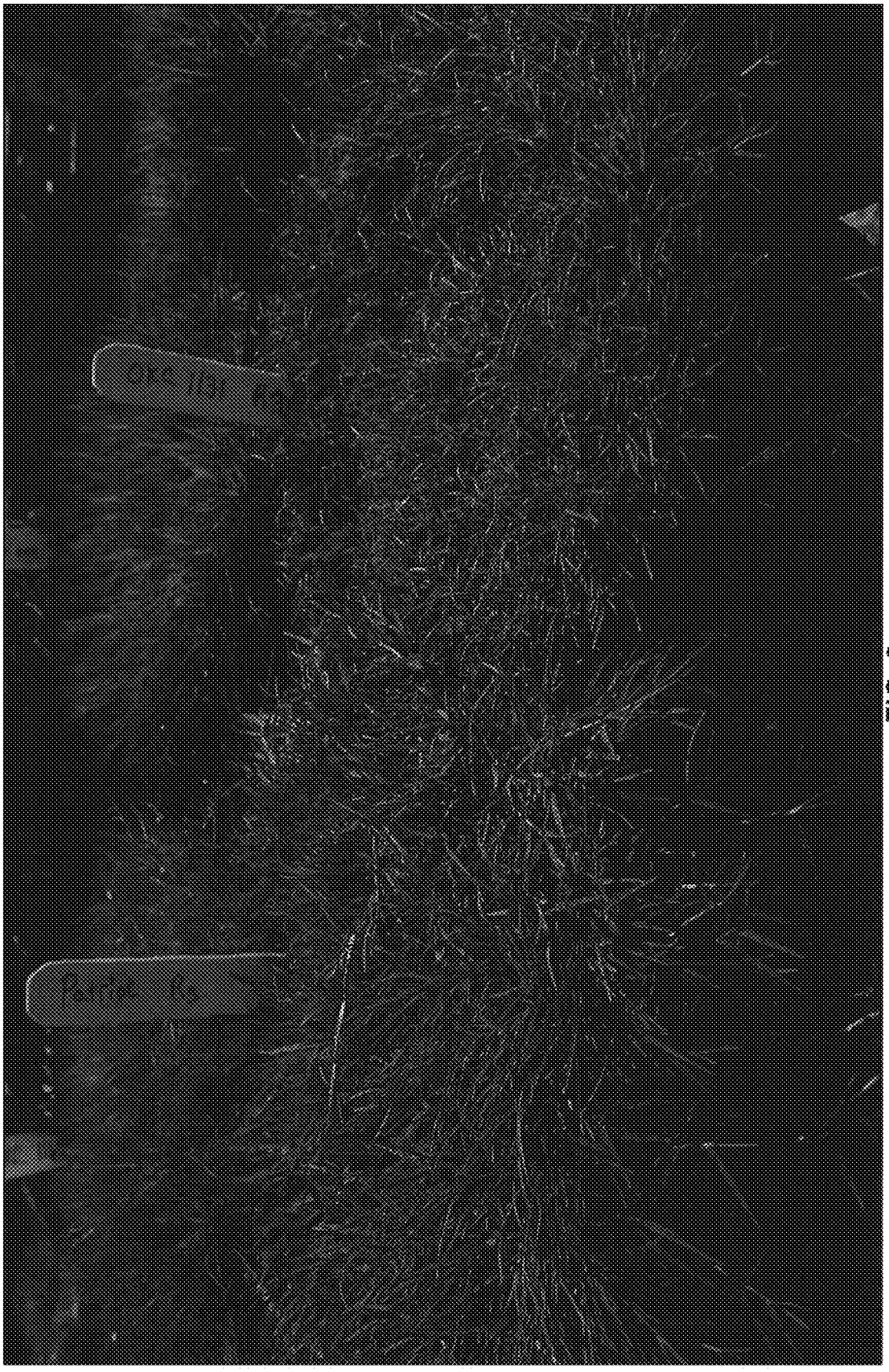
FIG. 3 is a comparative of mature growth 'OKC 1131' (right) to 'PATRIOT' (left).
Figure 4:
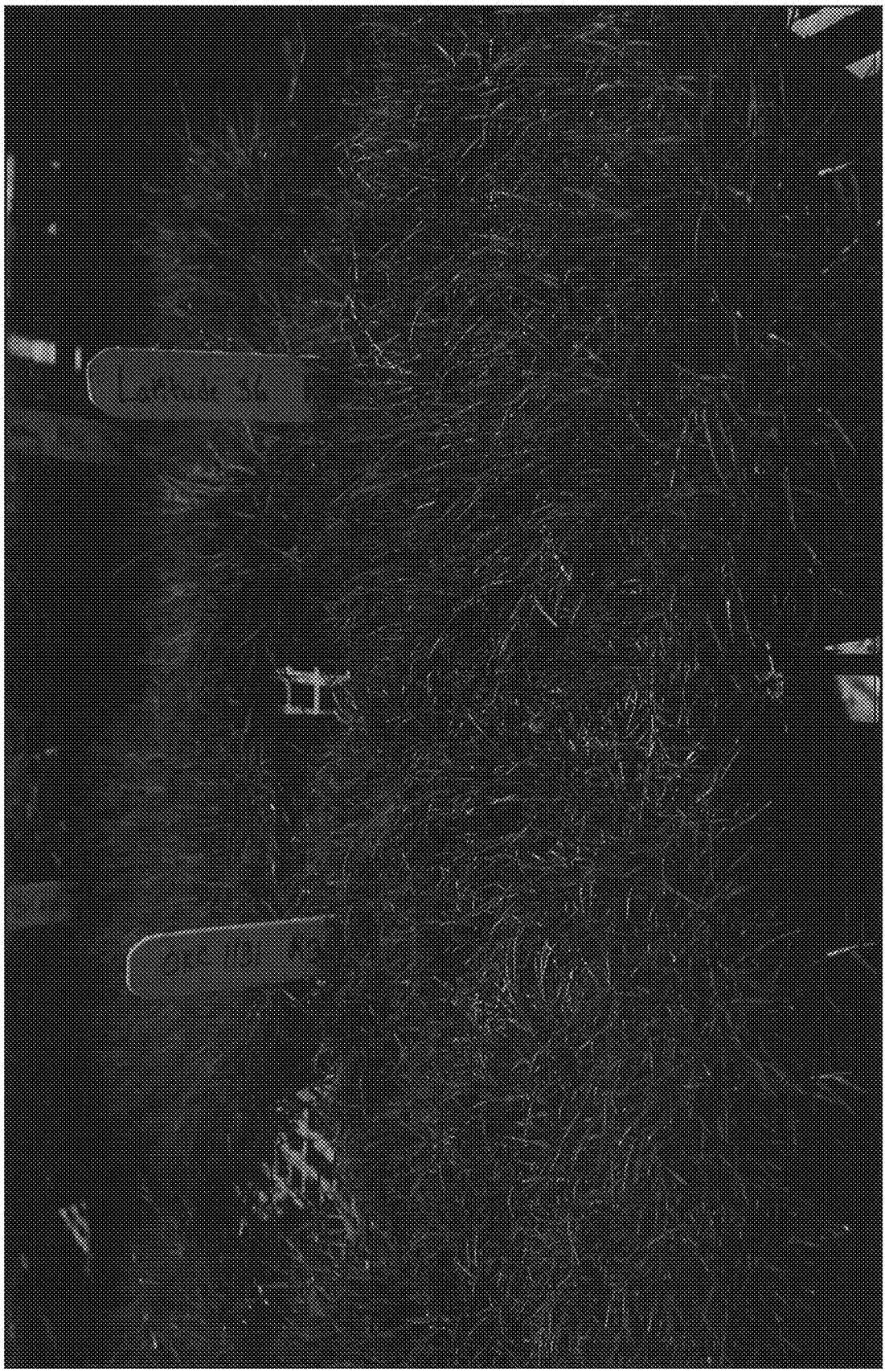
FIG. 4(1) is a comparative of mature growth 'OKC 1131' (left) to 'LATITUDE 36' (right).

'OKC 1131's' morphological characteristics for mature plants grown in a greenhouse are found in Table 1. 'OKC 1131's' leaf blade width, leaf blade length, internode length, and internode diameter were measured on potted plants of 'OKC 1131', 'Latitude 36', 'Northbridge', 'Patriot', 'Tifway', and 'Tifton 10' bermudagrasses. Measurements were collected from three replications of each cultivar with 20 subsamples for each replication in 2014. 'OKC 1131's' leaf blade width was found to be similar to that of 'NorthBridge' and 'Tifway' (FIG. 1), narrower than that of 'Tifton 10' (FIG. 2) and 'Patriot' (FIG. 3), but wider than that of 'Latitude 36' (FIG. 4). 'OKC 1131's' leaf blade length was found to be similar to that of 'Patriot',0 but shorter relative to 'NorthBridge', 'Tifway', and 'Tifton 10'. 'OKC 1131' had an internode length similar to that of 'Patriot', but shorter than that of 'Latitude 36', 'NorthBridge', 'Tifway', and 'Tifton 10'. 'OKC 1131's' internode diameter was larger than that of 'Tifway', similar to that of 'Latitude 36' and 'NorthBridge', but much narrower than that of 'Patriot' and 'Tifton 10'. The color of the internodes of 'OKC 1131' is relatively purple when exposed to sunlight. 'OKC 1131's' culm is similar in color to its leaves (i.e., color 144A on The R.H.S. Colour Chart). The length of 'OKC 1131's' culm is in a range of from about 10 cm to about 15 cm, with an average length of about 12 cm (which is the shortest among commonly-used turf bermudagrass cultivars). The leaf sheath of 'OKC 1131' is round and green and the average length of the auricle hairs is about 1.5 mm. Tables 1 and 2 provide data on 'OKC 1131's' leaf blade width and length. The surface texture of the 'OKC 1131' leaf is smooth and it has a flat point leaf tip and a folded vemation. 'OKC 1131's' collar type is continuous and its ligule comprises a ring of short and white hairs, each hair being less than about 0.5 mm long. 'OKC 1131's' inflorescence comprises one whorl having about 3 to about 4 racemes.

TABLE 1

2014 Measurements of leaf blades and internodes on shoots of the above listed potted plants grown in a greenhouse at the OSU Agronomy Research Station, Stillwater, Oklahoma.

| Cultivar | $4^{th}$ leaf blade* width (mm) | $4^{th}$ leaf blade length (cm) | $2^{nd}$ internode length (cm) | $2^{nd}$ internode diameter (mm) |
|---|---|---|---|---|
| OKC 1131 | 1.96 | 3.68 | 1.21 | 0.97 |
| Latitude 36 | 1.83 | 4.73 | 1.61 | 0.91 |
| NorthBridge | 1.92 | 5.72 | 1.63 | 0.95 |
| Patriot | 2.47 | 3.97 | 1.40 | 1.64 |
| Tifway | 1.97 | 5.41 | 2.42 | 0.84 |
| Tifton 10 | 2.98 | 4.42 | 1.28 | 1.69 |
| 5% LSD | 0.08 | 0.40 | 0.21 | 0.07 |

*From shoot apex.

'OKC 1131's' morphological characteristic measurements for mature plants grown in field plots are found in Table 2. The field plots were established in a randomized complete block design with three replications at the Oklahoma State University Agronomy Research Station, Stillwater, Okla. on May 6, 2014, and at the Oklahoma State University Cimarron Valley Research Station, Perkins, Okla. on May 12, 2014. Data were collected on 10 subsamples of each replication for each cultivar in July 2015, which measured the leaf blade width, leaf blade length, internode length, and internode diameter of 'OKC 1131'. The leaf blade width of 'OKC 1131' was found to be wider than that of 'Latitude 36' at Stillwater but similar to that of 'Latitude 36' at Perkins, similar to that of 'NorthBridge' and 'Tifway', but much narrower than that of 'Patriot' and 'Tifton 10' at the two locations (Table 2). 'OKC 1131' had shorter leaf blades and shorter internodes than all commercial cultivars at both locations. 'OKC 1131' had internode diameters similar to 'Latitude 36' and 'NorthBridge', smaller than 'Patriot' and 'Tifton 10', but larger than 'Tifway'.

TABLE 2

July 2015 leaf blade and internode data collected from shoots of the above listed field-grown plants.

| Location | Cultivar | $4^{th}$ leaf blade* width (mm) | $4^{th}$ leaf blade length (cm) | $2^{nd}$ internode length (cm) | $2^{nd}$ internode diameter (mm) |
|---|---|---|---|---|---|
| Stillwater, OK | OKC 1131 | 1.96 | 4.09 | 1.03 | 0.65 |
| | Latitude 36 | 1.84 | 4.94 | 1.46 | 0.60 |
| | NorthBridge | 1.91 | 6.12 | 2.07 | 0.63 |
| | Patriot | 2.28 | 5.09 | 1.62 | 1.03 |
| | Tifway | 1.91 | 5.25 | 2.39 | 0.54 |
| | Tifton 10 | 3.07 | 5.34 | 1.61 | 1.25 |
| | 5% LSD | 0.11 | 0.55 | 0.26 | 0.08 |
| Perkins, OK | OKC 1131 | 1.90 | 4.74 | 1.27 | 0.63 |
| | Latitude 36 | 1.96 | 5.31 | 1.57 | 0.65 |
| | NorthBridge | 1.98 | 6.84 | 1.83 | 0.70 |
| | Patriot | 2.28 | 5.51 | 1.71 | 1.10 |
| | Tifway | 2.04 | 6.49 | 2.23 | 0.53 |
| | Tifton 10 | 3.12 | 6.55 | 1.74 | 1.41 |
| | 5% LSD | 0.12 | 0.53 | 0.22 | 0.08 |

'OKC 1131' is highly infertile, thus must be vegetatively propagated.

NATIONAL TURFGRASS EVALUATION PROGRAM (NTEP) NATIONAL BERMUDAGRASS TEST

The detailed major performance characteristics of 'OKC 1131' presented herein were produced from the National Turfgrass Evaluation Program (NTEP) National Bermudagrass Test.

Establishment Rate: the NTEP test reported establishment rate data in 2013 (Table 3). 'OKC 1131's' was found to have excellent establishment ratings at each location. 'OKC 1131' was found to have an establishment rate similar to 'Celebration' and 'Patriot' but a quicker rate than 'Latitude 36', 'TifTuf', and 'Tifway' in a traffic trial located in Kentucky. In the Kentucky regular trial, 'OKC 1131' also had a similar establishment rate as 'Patriot' but quicker than three standard cultivars and 'TifTuf'. The Alabama performance of 'OKC 1131' found the establishment rate of 'OKC 1131' was similar to that of 'TifTuf' and 'Patriot' but quicker than that of 'Latitude 36', 'Celebration', and 'Tifway'. 'OKC 1131' was found to be similar in establishment rate to 'Celebration', 'TifTuf', and 'Patriot' but quicker than 'Latitude 36' and 'Tifway' in Florida and North Carolina. In Georgia, Indiana, the Tennessee regular trial, and Texas, 'OKC 1131's' establishment rates were similar to the four standard cultivars and 'TifTuf'. However, in the Tennessee traffic trial, 'OKC 1131' had similar establishment rates to 'Celebration', 'Patriot' and 'Latitude 36' but a quicker rate than 'TifTuf' and 'Tifway'. In the Kansas and Virginia tests, 'OKC 1131' was found to have a slower establishment rate than 'Patriot' but similar to 'TifTuf' and the three other standard cultivars (Celebration, Latitude 36, and Tifway). 'OKC 1131's' establishment rate was found to be similar to 'TifTuf', 'Patriot', 'Celebration', and 'Latitude 36' but quicker rate than 'Tifway' in the Missouri NTEP test. The Mississippi NTEP test results found that the establishment rate of 'OKC 1131' was similar to 'Celebration', 'Patriot', and 'TifTuf' but quicker than 'Latitude 36' and 'Tifway'. The Oklahoma test results found that 'OKC 1131' had an establishment rate similar to 'TifTuf' and 'Celebration' but quicker establishment rate than 'Tifway', 'Patriot', and 'Latitude 36'.

TABLE 3

2013 NTEP Establishment Rate Data

| NTEP Location | Slower Establishment Rate | Similar Establishment Rate | Quicker Establishment Rate |
|---|---|---|---|
| Kentucky (Regular Trial) | | Patriot | Latitude 36, TifTuf, and Tifway, Celebration |
| Kentucky (Traffic Trial) | | Celebration, Patriot | Latitude 36, TifTuf, and Tifway |
| Alabama | | TifTuf and Patriot | Latitude 36, Celebration, and Tifway |
| Florida | | Celebration, TifTuf, Patriot | Latitude 36 and Tifway |
| North Carolina | | Celebration, TifTuf, Patriot | Latitude 36 and Tifway |
| Georgia | | Latitude 36, Tifway, Patriot, Celebration, TifTuf | |
| Indiana | | Latitude 36, Tifway, Patriot, Celebration, TifTuf | |
| Tennessee (Regular Trial) | | Latitude 36, Tifway, Patriot, Celebration, TifTuf | |
| Tennessee (Traffic Trial) | | Latitude 36, Celebration, Patriot | TifTuf, Tifway |
| Texas | | Latitude 36, Tifway, Patriot, Celebration, TifTuf | |
| Kansas | Patriot | TifTuf, Latitude 36, Celebration, Tifway | |

TABLE 3-continued

2013 NTEP Establishment Rate Data

| NTEP Location | Slower Establishment Rate | Similar Establishment Rate | Quicker Establishment Rate |
|---|---|---|---|
| Virginia | Patriot | TifTuf, Latitude 36, Celebration, Tifway | |
| Missouri | | TifTuf, Patriot, Celebration, Latitude 36 | Tifway |
| Mississippi | | Celebration, Patriot, TifTuf | Latitude 36, Tifway |
| Oklahoma | | TifTuf, Celebration | Tifway, Patriot, Latitude 36 |

Turf Quality: 'OKC 1131' produces a high quality turf surface as indicated by the visual ratings of turf quality (NTEP field trial test data). The mean turf quality of 'OKC 1131' was in the top performing statistical group in both 2014 and 2015 via the 2013-2014 Progress Report and 2015 Progress Report (NTEP, 2015 & 2016), with a 2014 mean turf quality rating of 6.5 and a 2015 mean turf quality rating of 6.6 (Table 4).

'OKC 1131' is relatively stable in turfgrass quality performance across environments and finished in the top 25% of all trial entries at 78.6% of the test locations in 2015.

TABLE 4

2014 and 2015 NTEP Field Trial Test Turf Quality Data.

| | OKC 1131 | TifTuf | Tifway | Celebration | Patriot | Latitude 36 |
|---|---|---|---|---|---|---|
| 2014 Turf Quality | 6.5* | 6.6* | 5.9* | 5.5* | 6.0* | 6.4* |
| 2015 Turf Quality | 6.6* | 6.7* | 5.8* | 5.2* | 6.1* | 6.3* |

*Measured on a scale of 1-9, 9 being maximum quality.

Genetic Color: NTEP test data illustrated the average genetic color ratings of 'OKC 1131' as 7.2 in 2014 and 7.1 in 2015 (Table 5). Genetic color ratings are measured on a scale of 1-9, wherein 9 is the maximum dark green color. The 2014 NTEP test result data indicated that the genetic color rating of 'OKC 1131' was statistically similar to that of 'TifTuf' and 'Latitude 36' and less than 'Tifway', 'Celebration', and 'Patriot' (Table 5). The 2015 NTEP test result data indicated that genetic color ratings of 'OKC 1131' was statistically similar to 'Patriot' and greater than 'TifTuf', 'Tifway', 'Celebration' and 'Latitude 36' (Table 5).

TABLE 5

NTEP Genetic Color Test Data.

| | OKC 1131 | TifTuf | Tifway | Celebration | Patriot | Latitude 36 |
|---|---|---|---|---|---|---|
| 2014 Genetic Color Rating | 7.2* | 7.1* | 7.6* | 7.7* | 7.4* | 7.1* |
| 2015 Genetic Color Rating | 7.1* | 6.6* | 6.7* | 6.6* | 7.2* | 6.7* |

*Measured on a scale of 1-9, 9 being maximum dark green color.

Leaf texture: The 2014 NTEP trial data illustrates 'OKC 1131' overall mean leaf texture rating (7.4) was statistically the same as that of 'Latitude 36' (7.6), 'TifTuf' 7.1), and 'Tifway' (7.3) but finer than 'Patriot' (6.5) and 'Celebration' (6.1) (Table 6). The 2015 NTEP trial data illustrated that the leaf texture of 'OKC 1131' (6.5) was statistically the same as that of 'Latitude 36' (6.7) and 'TifTuf' (6.3) but finer than 'Tifway' (6.0), 'Patriot' (6.0), and 'Celebration' (5.3) (Table 6).

TABLE 6

NTEP Leaf Texture Test Data.

| | 'OKC 1131' | TifTuf | Tifway | Celebration | Patriot | Latitude 36 |
|---|---|---|---|---|---|---|
| 2014 Leaf Texture Ratings | 7.4* | 7.1* | 7.3* | 6.1* | 6.5* | 7.6* |
| 2015 Leaf Texture Ratings | 6.5* | 6.3* | 6.0* | 5.3* | 6.0* | 6.7* |

*Measured on a scale of 1-9, 9 = very fine.

Density: Mean stand density and mean percent living ground cover of 'OKC 1131' as indicated by ratings was found to have a very high density and living ground cover (LGC) in the NTEP trials. Density is the overall visual effect of the number of living plants per unit area of turfgrass canopy. The 2014 and 2015 NTEP trial data showed that the density of 'OKC 1131' in spring, summer and fall was similar to that of 'Tifway' in all six events, 'TifTuf' and 'Latitude 36' in five events, 'Celebration' in two events, and 'Patriot' in one event. 'OKC 1131' was found to have better density ratings than 'Patriot' in five events and 'Celebration' in four events. 'OKC 1131' was found to have a lower density rating than 'Latitude 36' and 'TifTuf' for one event (Table 7).

TABLE 7

Density Ratings.

| | OKC 1131 | Tifway | TifTuf | Latitude 36 | Celebration | Patriot |
|---|---|---|---|---|---|---|
| Spring 2014 Density | 6.3* | 6.9* | 7.1* | 7.0* | 6.6* | 6.3* |
| Summer 2014 Density | 7.5* | 7.2* | 7.7* | 7.6* | 6.3* | 6.9* |
| Fall 2014 Density | 7.7* | 7.4* | 7.7* | 7.5* | 7.1* | 6.8* |
| Spring 2015 Density | 7.1* | 6.8* | 6.9* | 6.8* | 5.5* | 6.3* |
| Summer 2015 Density | 7.2* | 7.1* | 7.4* | 7.3* | 6.3* | 6.7* |
| Fall 2015 Density | 7.3* | 7.1* | 7.3* | 7.3* | 6.9* | 6.7* |

*Measured on a scale of 1-9, 9 = maximum density.

Figure 5:
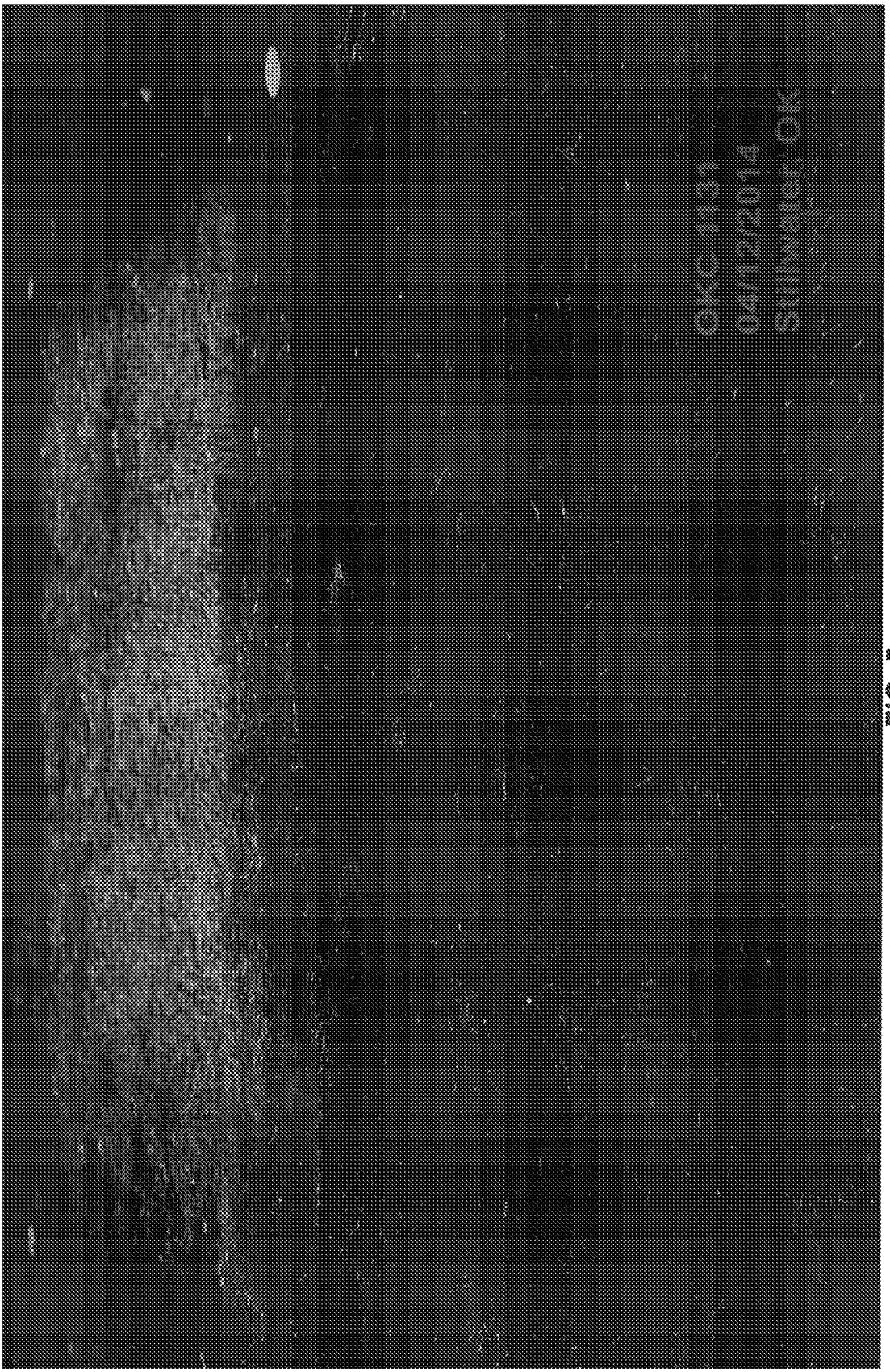
FIG. 5 is a comparative of spring greenup of mature growth 'OKC 1131' (bottom) to 'NUMEX SAHARA' (top) in field plots.

Spring Greenup: On the NTEP trial data scale, 1-9, wherein 9 equals the maximum greenup. The 2014 NTEP trial data showed the average spring greenup rating of 'OKC 1131' was a 6.1 (Table 8). The 2015 NTEP trial data found 'OKC 1131's' spring greenup rating to be a statistically similar 6.0 (Table 8). Spring greenup ratings reflect the comparative winter hardiness of 'OKC 1131' (FIG. 5).

TABLE 8

NTEP Spring Greenup Trial Data.

| | OKC 1131 | TifTuf | Tifway | Celebration | Patriot | Latitude 36 |
|---|---|---|---|---|---|---|
| 2014 Spring Greenup Rating | 6.1* | 5.2* | 4.1* | 3.7* | 4.8* | 5.3* |
| 2015 Spring Greenup Rating | 6.0* | 5.6* | 4.7* | 4.5* | 4.5* | 5.4* |

*Measured on a scale of 1-9, 9 indicates maximum greenup.

Drought Resistance: 'OKC 1131' was tested in a field trial at College Station, Tex., from August to October 2015. NTEP test data indicate 'OKC 1131' was one of the two top performers along with 'TifTuf'. The mean turf quality of 'OKC 1131' was found to be 6.9, whereas 'TifTuf' was discovered to be 7.5; however, 'OKC 1131' was found to be statistically superior to the other four standard cultivars. Additionally, during the drought test, 'OKC 1131's' percent living ground coverage (LGC) was indicated to be the same as 'TifTuf' for eight of twelve events, inferior for three events, but superior for one event. 'OKC 1131' exhibited better LGC than 'Latitude 36' for nine events, and better than 'Patriot' and 'Celebration' for three events. 'Patriot' had better LGC than 'OKC 1131' on one date during the duration of the drought test. Turfgrass quality and other ratings in this category were measured on a scale of 1-9; a measurement of 9 indicated the best turfgrass quality.

Further, a field trial was conducted at the Oklahoma State University Turfgrass Research Center, Stillwater, Okla., to determine water use rates of ten well-watered bermudagrass (*Cynodon* spp.) genotypes. The experiment was a randomized complete block design with three replications and it used mini-lysimeters with calcined clay as rooting media for water use rate measurement. Daily evapotraspiration (ET) rates were measured at pre-dawn by weighing the mini-lysimeters every twenty-four hours for ten dates in 2013, six dates in 2014, and eight dates in 2015.

The results of the daily ET transpiration rate measurements for 2013 indicated that 'TGS-U3', 'TifTuf', and 'Premier' (described and claimed in U.S. Plant Pat. No. 18,247) used more water than OKC 1302, OKC 1163, 'Latitude 36', 'Tifway', and 'OKC 1131'. The 2014 data indicated that 'TifTuf', 'Celebration', 'Tifway', and OKC 1302 used more water than 'Premier', 'TGS-U3', 'NorthBridge', 'OKC 1163', and OKC '1131'. The 2015 testing data indicated that 'TifTuf', 'Celebration', and 'Latitude 36' used more water than 'Premier', 'OKC 1302', 'OKC 1163', 'OKC 1131', and 'NorthBridge'.

The testing data illustrated the ET rates in 2013 ranged from 4.14 to 4.74 mm $d^{-1}$; the ET rates in 2014 ranged from 4.45 to 5.19 mm $d^{-1}$; the ET rates in 2015 ranged from 3.60 to 5.15 mm $d^{-1}$. 'OKC 1131' used 18.0% or 0.89 mm $d^{-1}$ less water than 'TifTuf'.

Winterkill: 'OKC 1131' has good winter hardiness relative to other turf bermudagrass cultivars as indicated by the NTEP data results. Its tolerance of lower temperatures during winter reduces risk of winter injury relative to less winter hardy cultivars when grown in colder climatic regions where bermudagrass is used. Winterkill rate is calculated on a scale of 0-99%, where 99% indicates a complete kill. Data from the Lexington, Ky. NTEP test site indicated that 'OKC 1131' had the lowest winterkill rating of 25.0%. 'Tifway' had a winterkill rating of 99.0%, 'Celebration' illustrated a winterkill rating of 98.7%, 'TifTuf' had a winterkill rating of 94.0%, 'Latitude 36' had a winterkill rating of 73.3%, and 'Patriot' had a winterkill rating of 50.0%. The winterkill data from the West Lafayette, Ind. NTEP test site further illustrated the improved winter hardiness (lower winterkill rating) of 'OKC 1131'. 'OKC 1131' had a winterkill rating of 4.0%, 'Tifway' had a winterkill rating of 98.0%, 'Celebration' had a winterkill rating of 97.3%, 'TifTuf' had a winterkill rating of 82.7%, 'Latitude 36' had a winterkill rating of 41.3%, and 'Patriot' indicated a winterkill rate of 11.7%.

Frost tolerance: Data from the NTEP test sites indicated that 'OKC 1131' had a frost tolerance rating (5.3) which was statistically the same as that of the four standard cultivars and 'TifTuf'. Frost tolerance was rated on a scale of 1-9, 9 indicated frost injury is absent, i.e., maximum frost tolerance.

Seedhead Rating: 2014 NTEP test data indicated that 'OKC 1131' had a lower seedhead rating (6.5) than 'Latitude 36' (8.0), but similar to 'Tifway' (7.3), 'TifTuf' (7.0), 'Patriot' (6.8), and 'Celebration' (6.7). The 2015 NTEP test data indicated that the seedhead rating (4.9) of 'OKC 1131' was statistically the same as 'Celebration' (5.8), but lower than the other four cultivars. Seedhead ratings were measured on a scale of 1-9; a measurement of 9 indicated no seedheads were present.

Insect Damage/Disease Response/Nematode Response: There were no reports or observations of any unusual and/or severe insect damage on bermudagrass entries including 'OKC 1131' in the 2013-2018 NTEP trial. The leaf spot disease rating (2.0) in 'OKC 1131' was lower than in 'Tifway' (8.3), 'TifTuf' (8.0), and 'Latitude 36' (8.0) in 2014; however, OKC 131 had a leaf spot disease incident rating similar to 'Patriot' (5.3) and 'Celebration' (4.0). In 2014 and 2015, the data for dollar spot disease indicated that 'OKC 1131' rated as being not statistically different from the four standard cultivars and 'TifTuf'. Further, the 2013-2018 NTEP Gainesville, Fla. field trial data indicated that the nematode response of 'OKC 1131' was similar to the four standard cultivars and 'TifTuf'. Leaf spot and dollar spot ratings were measured on a scale of 1-9; a measurement of 9 indicated no disease.

Salinity response field data indicate 'OKC 1131' was the top performer among the bermudagrass entries and had a better leaf firing rating than 'Tifway', but not different from 'Celebration' when tested in culture at 45 dS $m^{-1}$. Salinity response was measured via electrical conductivity, in one greenhouse experiment located in College Station, Tex., where 10 experimental bermudagrasses and two standards, 'Celebration' and 'Tifway', were tested. In the salinity response field testing, 'OKC 1131' was tested under the experimental name 'OSUB11-31'.

Traffic tolerance: The 2015 NTEP traffic trial data for two locations (Lexington, Ky. and Knoxville, Tenn.) were utilized for the traffic tolerance assessment. The data indicated that 'OKC 1131' has traffic tolerance similar to 'Tifway', 'TifTuf', 'Patriot', and 'Latitude 36', except 'OKC 1131' performed better than 'Celebration' at the Lexington, Ky. site.

Herbicide tolerance: 'OKC 1131' did not display any herbicide injury symptoms during the applications of Ronstar 2G (oxidiazon) and Strike Three (2, 4-D+MCPP+dicamba) during both the dormant and periods of active growth. 'OKC 1131' did not display any injury symptoms in the spring following applications of glyphosate when applied at 24-32 fluid ounces during the dormant season for winter annual weed control. A replicated field trial was established in a randomized complete block design with three replications at the Oklahoma State University Turfgrass Research Center at Stillwater, Okla., to test cultivar tolerance to the following post-emergence herbicides at one and three times the label rates during spring and summer sessions: Triplet (2, 4-D+MCPP+dicamba), MSM (metsulfuron-methyl), Drive XLR8 (quinclorac), and Monument 75WG (Trifloxysulfuron-sodium). Treatments were applied on May 5, 2017 with non-ionic surfactant (Triplet, MSM, Monument 75DG) or methylated seed oil (Drive XLR8 in accordance with label recommendations. For each treatment combination, 'OKC 1131' demonstrated similar or reduced injury in comparison to 'Tifway' in both seasons. At three times label rate, both cultivars showed mild and ephemeral injury symptoms using Drive XLR8 or Triplet (Table 3). Monument 75WG and MSM did not result in substantial injury for either cultivar at the three times label rate.

Sod Tensile Strength and Handling Quality: 'OKC 1131' was indicated to have sod tensile strength values lower than 'Tifway', similar to 'NorthBridge' and 'Latitude 36', but higher than 'Midlawn' in a replicated field trial. Further, 'OKC 1131' was found to possess a sod handling quality similar to that of 'Latitude 36' 'NorthBridge' and 'Tifway' and a higher sod handling quality than 'Midlawn'. The NTEP trial located at Stillwater, Okla., was used to measure the sod tensile strength and to rate the sod handling quality. 'OKC 1131' was found to have acceptable sod handling quality and was found to have lower sod handling strength relative to other bermudagrass cultivars. Further sod tensile strength testing occurred on a sod farm in Oklahoma. The on-farm trial indicated 'OKC 1131' had sufficient sod strength for harvest by standard sod farm harvest equipment.

'OKC 1131' has low vertical growth relative to other industry standard cultivars and other OSU experimental genotypes as seen in a 2014 replicated field trial to evaluate the vertical growth rate of bermudagrass. The 2015 results indicate that 'OKC 1131' had the lowest vertical growth rate of all the industry standards tested. The 2016 data results indicated 'OKC 1131' had a vertical growth rate similar to 'Tifway', 'Latitude 36', and 'NorthBridge' and 'OKC 1131' illustrated a lower vertical growth rate compared to 'Midlawn'.

Figure 6:
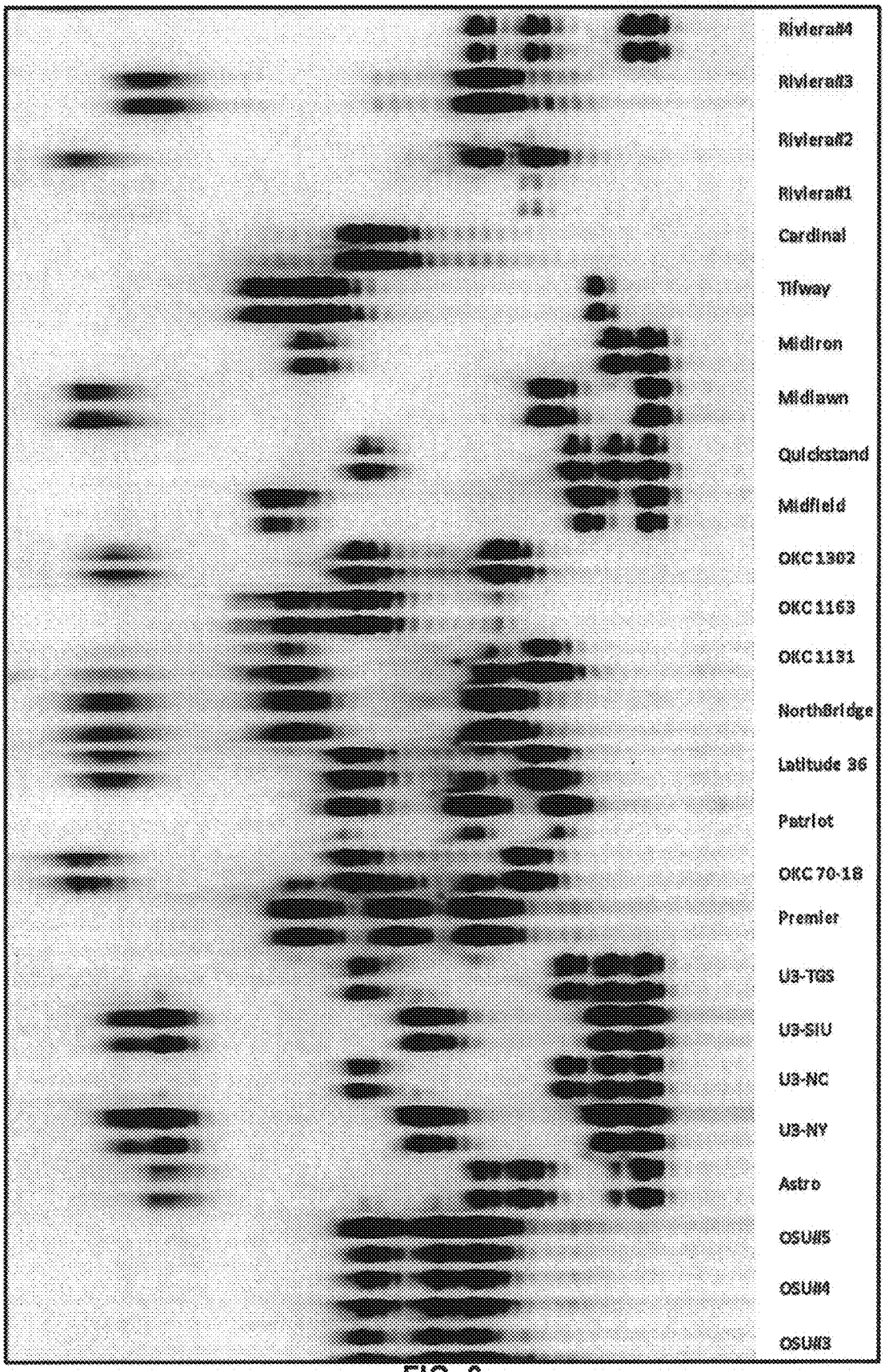
FIG. 6 illustrates a gel image of the DNA profile of 'OKC 1131' and 31 other turf bermudagrass genotypes using a SSR (simple sequence repeat) marker CACD 3132. The bermudagrass designations are given at the right of the gel image.

'OKC 1131' can be distinguished from other cultivars by DNA profiling. FIG. 6 shows a gel image of DNA profiles of 32 turf bermudagrass genotypes including 'OKC 1131' amplified by a simple sequence repeat (SSR) marker CAC 3132 (Fang et al., 2015), such bermudagrass genotypes and varieties including, but not limited to, 'Premier' (disclosed and claimed in U.S. Plant Pat. No. 18,247), 'Midfield' (described and claimed in U.S. Plant Pat. No. 8,168), and 'Midlawn' (described and claimed in U.S. Plant Pat. No. 8,162).

What is claimed is:

1. A new and distinct variety of turf bermudagrass, substantially as illustrated and described herein.

* * * * *